(12) United States Patent
Gemert et al.

(10) Patent No.: US 8,246,990 B2
(45) Date of Patent: Aug. 21, 2012

(54) HYDROGEN BONDED HYDROGELS

(75) Inventors: Gaby Maria Leonarda Hoorne-Van Gemert, Landgraaf (NL); Henricus Marie Janssen, Eindhoven (NL); Egbert Willem Meijer, Waalre (NL); Anton Willem Bosman, Eindhoven (NL)

(73) Assignee: Suprapolix B.V., Eindhoven (NL)

( * ) Notice: Subject to any disclaimer, the term of this patent is extended or adjusted under 35 U.S.C. 154(b) by 621 days.

(21) Appl. No.: 11/913,466

(22) PCT Filed: May 3, 2006

(86) PCT No.: PCT/NL2006/050106
§ 371 (c)(1),
(2), (4) Date: Nov. 2, 2007

(87) PCT Pub. No.: WO2006/118460
PCT Pub. Date: Nov. 9, 2006

(65) Prior Publication Data
US 2009/0004274 A1     Jan. 1, 2009

Related U.S. Application Data

(60) Provisional application No. 60/679,649, filed on May 11, 2005.

(30) Foreign Application Priority Data

May 4, 2005   (EP) .................................. 05103763

(51) Int. Cl.
*A61K 9/00*      (2006.01)
*C08L 101/02*    (2006.01)

(52) U.S. Cl. ......... 424/486; 526/257; 526/258; 528/367

(58) Field of Classification Search ........................ None
See application file for complete search history.

(56) References Cited

U.S. PATENT DOCUMENTS

| | | |
|---|---|---|
| 4,942,035 A | 7/1990 | Churchill et al. |
| 5,548,035 A | 8/1996 | Kim et al. |
| 5,883,211 A | 3/1999 | Sassi et al. |
| 6,320,018 B1 | 11/2001 | Sijbesma et al. |
| 6,803,447 B2 | 10/2004 | Janssen et al. |
| 6,818,018 B1 | 11/2004 | Sawhney |
| 6,972,304 B2 | 12/2005 | Smith et al. |
| 2004/0034190 A1 | 2/2004 | Janssen et al. |
| 2004/0220142 A1 | 11/2004 | Marciani |
| 2005/0031566 A1 | 2/2005 | Cooper et al. |

FOREIGN PATENT DOCUMENTS

| | | |
|---|---|---|
| EP | 1 213 309 A | 6/2002 |
| WO | WO-99/07343 A1 | 2/1999 |
| WO | WO-02/46260 A1 | 6/2002 |
| WO | WO-03/032929 A2 | 4/2003 |
| WO | WO 03032929 A2 * | 4/2003 |
| WO | WO 03/099875 A | 12/2003 |
| WO | WO-2006/118460 A1 | 11/2006 |

OTHER PUBLICATIONS

Lange, J. Polymer Science: Part A, vol. 37, No. 19, 1999.*
Hirschberg et al., "Ureidotriaziane-based Supramolecular Copolymers," *Macromolecules*, 2003, pp. 1429-1432, vol. 36.
Folmer et al., "Supramolecular Polymer Materials: Chain Extension of Telechelic Polymers Using a Reactive Hydrogen-Bonding Synthon," *Advanced Materials*, Jun. 16, 2000, pp. 874-878, vol. 12, No. 2, Wiley VCH, Weinheim, Germany.
Lange et al., "Hydrogen-Bonded Supramolecular Polymer Networks," *Journal of Polymer Science, Polymer Chemistry Edition*, 1999, pp. 3657-3670, vol. 37, Interscience Publishers, New York, NY, US.

* cited by examiner

*Primary Examiner* — Robert A Wax
*Assistant Examiner* — William Craigo
(74) *Attorney, Agent, or Firm* — Gilberto M. Villacorta; Sunit Talapatra; Foley & Lardner LLP

(57) ABSTRACT

The present invention relates to new hydrogel materials using water gellants that are comprised by hydrophilic polymers to which hydrogen bonding units are covalently attached. Optionally, the hydrogel contains additional ingredients or additives. These new reversible hydrogels can easily be fine-tuned in their mechanical performance and functionality and are especially suitable for cosmetic and biomedical applications.

14 Claims, No Drawings

HYDROGEN BONDED HYDROGELS

FIELD OF THE INVENTION

This invention relates to new hydrogel materials that consist of water gellants comprising hydrophilic polymers to which hydrogen bonding units are covalently attached so that they are physically or non-covalently cross-linked in a reversible supramolecular way by hydrogen bonds. As the introduced water gellants are physically or non-covalently cross linked, the hydrogel materials are more easily processed. In addition, fine-tuning of the material properties of such a hydrogel (e.g. mechanical strength or elasticity, degradation behaviour) can be controlled more easily.

BACKGROUND OF THE INVENTION

Hydrogels can be characterized by three-dimensional networks of polymer chains that can reversibly be deformed. They absorb polar solvents such as water and they find applications in for example medical applications including bone transplants and tissue adhesives, drug delivery systems, cosmetics, pharmaceuticals and in water management.

Hydrogels can occur in the cross-linked form or in the uncross-linked form. Cross-linking usually provides higher viscosities due to an apparent or real increase of the molecular weight and often results into the formation of gels.

Cross-linking can be achieved chemically by the formation of covalent bonds or physically by the formation of e.g. hydrogen bonds or ionic interactions. Obviously, cross-linking can also be achieved both chemically and physically.

Chemical cross-linking of hydrophilic polymers is a general and often applied route to obtain hydrogels. In order to be able to administer or process these gels, prepolymers are dissolved in water and are then polymerized resulting in (in situ) hydrogel formation. Hydrogellation procedures are often based on the use of acrylic or methacrylic macromonomers that are not preferred in (biomedical) applications, because of their inherent toxicity and because they usually require an auxiliary, potentially hazardous, initiator for polymerization. Moreover, cross-linked hydrogels lack reversibility and are limited in their degradation behaviour, as poly (acrylates) and poly(methacrylates) are not biodegradable. For example, U.S. Pat. No. 5,410,016 discloses hydrogels based on copolymers of poly(ethylene glycol) with poly(DL-lactide) containing pendant acrylate functions that are cross-linked in situ. WO 01/44307 discloses hydrogels based on polyvinyl alcohol modified with pendant acrylate and methacrylate groups that are chemically cross-linked in situ. Hence, in both patents an irreversible cross-linked hydrogel is obtained by starting from water processable prepolymers that contain reactive groups.

Hydrogels based on natural polymers, especially collagen, are biocompatible and mostly thermally reversible (Mooney et al. Chem. Rev. 101, page 1869, 2001). However, the mechanical properties of these gels are limited and hardly, if at all, tunable. Especially the mechanical strength in these materials is too low, and often an additional chemical modification is required to make them stronger. However, this results in a reduced biocompatibility and a reduced biodegradation.

U.S. Pat. No. 4,942,035 and U.S. Pat. No. 5,548,035 disclose hydrogels based on block-copolymers in which hydrophilic blocks are alternated by hydrophobic blocks. For example, U.S. Pat. No. 4,942,035 discloses a triblock copolymer consisting of a polyethylene glycol middle block surrounded by two poly(D,L-lactide-co-glycolide) polyester blocks (weight ratio of polyester to PEG at least 1) was prepared and showed gelling behaviour in water. The hydrogels are formed because of phase separation of the hard hydrophobic polyester block, and consequently the relative amount of the hydrophobic polymer needs to be high to counterbalance the hydrophilicity of the polyethylene glycol block to guarantee the gelling behaviour. Therefore, the range of mechanical properties of these gels is limited—for examples with respect to the elasticity—as these properties are mainly governed by the hard block.

WO99/07343 discloses thermally reversible hydrogels intended for uses in drug delivery applications that are based on a hydrophilic polyethylene glycol block and hydrophobic PLLA (poly-L-lactic acid) blocks. The gelling is governed by the presence of the crystalline hard blocks formed by the PLLA. The presence of the crystalline PLLA-blocks limits the mechanical properties and the biodegradation of these materials to a great extent.

U.S. Pat. No. 6,818,018 discloses hydrogels that can be formed in a mammal in situ by providing a system comprising a first polymer that is capable to form physical cross-links and a second polymer that is capable to form chemical cross-links. The first polymer may be selected from a wide group of materials including ionomers whereas the second polymer may be selected from virtually any material that has chemical groups capable of forming covalent bonds.

U.S. Pat. No. 5,883,211 discloses a thermo-reversible hydrogel comprising an uncrosslinked copolymer based on poly(acrylamide) containing up to six different monomers with hydrogen bonding N-substituent groups. The relative content of these monomers with hydrogen bonding N-substituent groups in the uncrosslinked copolymer needs to be higher than 50% to display thermo-reversible gelling behaviour.

In general, "supramolecular chemistry" is understood to be the chemistry of physical or non-covalent, oriented, multiple (at least two), co-operative interactions. For instance, a "supramolecular polymer" is an organic compound that has polymeric properties—for example with respect to its rheological behaviour—due to specific and strong secondary interactions between the different molecules. These physical or non-covalent supramolecular interactions contribute substantially to the properties of the resulting material.

Supramolecular polymers comprising of (macro)molecules that bear hydrogen bonding units can have polymer properties in bulk and in solution, because of the hydrogen bridges between the molecules. Sijbesma et al. (see U.S. Pat. No. 6,320,018 and Science, 278, 1601) have shown that in cases where a self-complementary quadruple hydrogen bonding unit (4H-unit) is used, the physical interactions between the molecules become so strong that polymers with much improved material properties can be prepared.

Several telechelic polymers have been modified with 4H-units, as has been disclosed by Folmer, B. J. B. et al., Adv. Mater. 2000, Vol. 12, 874, in Hirschberg et al., Macromolecules 1999, Vol. 32, 2696, and in WO 02/46260. However, the behaviour and properties of the disclosed polymers in aqueous solution were not studied, and most presumably they do not dissolve in water or have little affinity with water due to their apolar backbones (for example, poly(ethylene butylene)s, polysiloxanes and polybutylene oxides have been prepared). Moreover, these polymers contain the 4H-unit only at the (two) termini of the polymer chain, limiting the mechanical properties of the resulting materials.

A poly(ethylene-propylene)oxide co-polymer (PEO-PPO-polymer) having three alcohol end groups was modified with 4H-units (cf. Lange et al. J. Polym. Sci. A, 1999, 3657 and WO02/098377). The modified polymer was soluble in organic solvents such as chloroform and THF and it appeared that the viscosity of the polymer was significantly effected by the polarity of the solvent. For example, addition of water to a solution of the polymer resulted in a significant decrease of the viscosity due to breaking of the hydrogen bonds between polymer molecules and formation of hydrogen bonds between polymer molecules and water molecules. However, the viscosity was still much higher than that of a solution comprising as reference a low molecular weight compound bearing one 4H-unit. Anyway, due to the relatively high PPO-content (63%) of the PEO-PPO copolymer, this material will hardly, if at all, dissolve in water and the polymers are also not tested in water.

U.S. Pat. No. 6,803,447, incorporated by reference herein for the US patent practice, discloses chemistry to acquire polymers with grafted quadruple H-bonding units. For example, polyacrylates and polymethacrylates with grafted 4H-units have been produced using different kinds of polymerization techniques. However, these polymers do not contain biodegradable components, and have not been tested in water.

WO 03/032929 discloses inter alia a non-biodegradable polysiloxane of which the backbone is functionalized with 4H-units. WO 03/032929 discloses also a polyethyleneoxide polymer comprising two 4H-units and a polyvinyl alcohol comprising about 5 to about 25 4H-units. These two latter polymers are for examples formulated in a styling gel comprising 0.4 wt % of a high molecular weight gelling agent (Carbopol 980), 3.8 wt. % of the polymer, and 84.6 wt. % water to which additionally 10 wt % ethanol as cosolvent is added (cf. Example 5) apparently in order to make these polymers processable.

EP A 1392222 discloses inter alia a telechelic poly(ethylene-propylene)oxide co-polymer (PEO-PPO-polymer) having three alcohol end groups that is modified with 4H-units resulting in a non-water processable polymer. Nevertheless, in example C of this patent a hairstyling gel is described with only 0.2 wt % of the PEO-PPO-polymer containing 4H-units, in an aqueous composition that further contains 1.0 wt % of a gelling agent based on cross-linked high molecular weight polyacrylate and 17 wt % ethanol as cosolvent. Apparently, the high ethanol content is needed to make the PEO-PPO polymer processable.

US 2003/0079644 discloses ink additives comprising 2-4 4H-units that are prepared from e.g. PEO-PPO polymers commercially available under the trade name VORANOL® from Dow Chemical Co., Midland, Mich., US, and 2(6-isocyanato-hexylaminocarbonylamino)-6-methyl-4(1H)-pyrimidone. According to the Examples XIII-XVI of US 2003/0079644, the ink compositions may comprise up to 5 wt. % of the polymer and water in the range of about 18 to about 35 wt. % and these compositions would have a viscosity at about 25° C. of no more than about 10 cP (cf. paragraphs [0174] and [0179] of US 2003/0079644). This implies that these polymers are not water gellants.

Because of the shortcomings of state-of-the-art hydrogels, there is a need for synthetic polymers that are able to gel water reversibly, implying that the hydrogels can be switched between a gelled state and a liquid state. This would facilitate easy processing and administration of these hydrogels. In addition, it is desired that hydrogels can be tuned with respect to their mechanical properties to be able to meet the requirements of specific applications. Also, it would be advantageous to be able to make biodegradable reversible hydrogels.

SUMMARY OF THE INVENTION

It is an object of the present invention to provide new hydrogels comprising a polymeric gellant, water and optionally another solvent and a process to prepare such new hydrogels. With this invention, easy preparation of hydrogels is enabled without the need for chemical cross-linking procedures, or the need for large hydrophobic blocks or crystalline domains in the structure of the gellant. The hydrogels according to the invention combine easy processing or administration with good and tunable mechanical properties, while it is optional to make the hydrogels biodegradable.

The present invention therefore relates to a hydrogel comprising:
(a) 0.3-50.0 wt. %, based on the total weight of the hydrogel, of a water gellant consisting of a hydrophilic polymer to which at least two 4H-units are covalently attached, wherein the 4H-unit has the general formula (1) or (2):

wherein the C—$X_i$ and the C—$Y_i$ linkages each represent a single or double bond, n is 4 or more, and $X_i$ represent donors or acceptors that form hydrogen bridges with the H-bridge forming monomeric unit containing a corresponding general form (2) linked to them with $X_i$ representing a donor and $Y_i$ an acceptor and vice versa; and
(b) 50.0 to 99.7 wt. % water.

DETAILED DESCRIPTION OF THE INVENTION

In this description and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

When investigating supramolecular hydrophilic polymers comprising quadruple hydrogen bonding units (4H-units), it was surprisingly found that these materials were able to gel water in a reversible way. In contrast to what was expected, the presence of the polar water molecules did not corrupt the strength of the hydrogen bonding interactions. As a consequence, a wide variety of hydrogels could be made with a variety of mechanical properties depending on the nature of the polymer backbone and the amount of 4H-units in the polymer. The reversibility of the supramolecular hydrogen bonding interaction allows for reversible switching between a gelled state and a liquid state by changing the temperature, the concentration of polymeric gellant, or the polarity or ionic strength of the solvent, and therefore makes it possible to easily process or administer the hydrogel for the desired application. Moreover, the reversible supramolecular interaction can also favour the biodegradation of the hydrogel material.

The 4H-Unit

It is preferred that in formulas (1) and (2) n equals 4 so and that the 4H-unit comprises four donors or acceptors $X_1 \ldots X_4$ and $Y_1 \ldots Y_4$. The 4H-unit may be self-complementary (i.e. the two hydrogen bonded units $X_1 \ldots X_4$ and $Y_1 \ldots Y_4$ have an equal array of donors and acceptors), or non self-complementary (i.e. the two hydrogen bonded units $X_1 \ldots X_4$ and $Y_1 \ldots Y_4$ have two different arrays of donors and acceptors). Preferably, the 4H-unit comprises two successive donors, followed by two successive acceptors, i.e. that it is preferred that $X_1$ and $X_2$ are donors and $X_3$ and $X_4$ are acceptors. Preferably, the donors and acceptors are O, S, and N atoms. The 4H unit is in detail disclosed in U.S. Pat. No. 6,320,018 which is incorporated by reference herein.

According to a preferred embodiment of the present invention the 4H-unit has the general formula (3) or formula (4) and tautomers thereof:

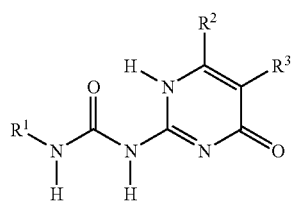

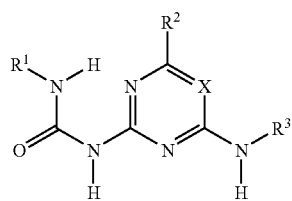

wherein X is nitrogen atom or a carbon atom bearing a substituent $R^{15}$, preferably X is a nitrogen, and wherein $R^1$, $R^2$, $R^{15}$ and $R^3$ are selected from the group consisting of:

(a) hydrogen;
(b) $C_1$-$C_{20}$ alkyl;
(c) $C_6$-$C_{12}$ aryl;
(d) $C_7$-$C_{12}$ alkaryl;
(e) $C_7$-$C_{12}$ alkylaryl;
(f) polyester groups having the formula (5)

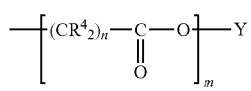

wherein $R^4$ and Y are independently selected from the group consisting of hydrogen and $C_1$-$C_6$ linear or branched alkyl, n is 1-6 and m is 10 to 100;

(g) $C_1$-$C_{10}$ alkyl groups substituted with 1-4 ureido groups according to the formula (6)

$$R^5\text{—NH—C(O)—NH—} \quad (6)$$

wherein $R^5$ is selected from the group consisting of hydrogen and $C_1$-$C_6$ linear or branched alkyl;

(h) polyether groups having the formula (7)

wherein Y, $R^6$ and $R^7$ are independently selected from the group consisting of hydrogen and $C_1$-$C_6$ linear or branched alkyl and o is 10-100; and wherein the 4H-unit is bonded to a polymer backbone via $R^1$, $R^2$ and/or $R^3$ (so that $R^1$, $R^2$ or $R^3$ represent a direct bond) with the other R groups representing, independently a side chain according to (a)-(h).

In a first preferred embodiment, the 4H-unit is bonded to a polymer backbone via $R^1$ (so that $R^1$ constitutes a direct bond), while $R^2$ and $R^3$ are independently any one of the groups (a)-(h) defined above, preferably group (b), more preferably 2-ethylpentyl or methyl and most preferably methyl. Most preferably, the 4H-unit is bonded to the polymer backbone via $R^1$, whereas $R^2$ is any one of the groups (a)-(h) defined above, more preferably group (b), even more preferably 2-ethylpentyl or methyl and most preferably methyl, and $R^3$ is hydrogen.

In a second preferred embodiment, the 4H-unit is bonded to a polymer backbone via $R^1$ and $R^2$ (so that $R^1$ and $R^2$ constitute direct bonds), while $R^3$ is any one of the groups (a)-(h) defined above, preferably group (a) or (b), more preferably group (a) or the 4H-unit is bonded to a polymer backbone via $R^1$ and $R^3$ (so that $R^1$ and $R^3$ constitute a direct bond), while $R^2$ is any one of the groups (a)-(h) defined above, preferably group (b), more preferably 2-ethylpentyl or methyl and most preferably methyl. Most preferably for this embodiment, the 4H-unit is bonded to a polymer backbone via $R^1$ and $R^3$, while $R^2$ is any one of the groups (a)-(h) defined above, preferably group (b), more preferably 2-ethylpentyl or methyl and most preferably methyl.

As will be apparent to the person skilled in the art, the groups (b)-(h) defined above may be linear, branched or cyclic where appropriate.

The Hydrophylic Polymer

The water gellant of the present invention preferably comprises 2-50 4H-units, more preferably 3-50, even more preferably 4-30, and most preferably 6-20 4H-units which are covalently bonded to the polymer backbone of a hydrophilic polymer.

According to this invention, a hydrophilic polymer is defined as a polymer having a solubility in water of at least 1 g/l. In addition, it is preferred that neither the hydrophilic polymer nor the water gellant comprises ionic groups as disclosed in WO 2005/042641.

The hydrophilic polymers used to prepare the water gellant can be comprised of hydrophilic polymers with different chemical natures and/or different molecular weights. The 4H-units can be attached to the hydrophilic polymer in any way, e.g. by grafting onto the hydrophilic polymer, by attachment to multiple end groups of the hydrophilic polymer, or the 4H-units can be an integral part of the backbone of the polymer that constitutes the water gellant. As will be understood by the person skilled in the art, the 4H-units may also be attached by a combination of these bonding modes.

According to a first preferred embodiment of the present invention, the hydrophilic polymer is a multifunctional polymer having a multitude of end-groups to which the 4H-units can be covalently grafted (partial or total modification). The water gellant according to this embodiment of the invention has a number average molecular weight of 1200-1,000,000, more preferably 2000-50000 and most preferably 7500-21000 Dalton.

According to a second preferred embodiment of the present invention, 4H-units can be (partial) end functionalized onto a hydrophilic homopolymer or a hydrophilic copolymer that is independently selected from the group consisting of telechelic polymers, functional star polymers, functional (hyper)branched polymers and functional dendritic polymers which have a multitude of functional end groups to which the 4H-units can be covalently attached. It is further preferred that the water gellant according to this second embodiment of the invention has a number average molecular weight of 1200-100,000, more preferably 2000-50000 and most preferably 7500-21000 Dalton.

According to a third preferred embodiment of the present invention, the water gellant is a block copolymer, wherein the hydrophilic polymer is alternated by the 4H-unit, either in a purely alternating fashion, or in a random fashion, or in any fashion in between these modes. In other words, the 4H-units form an integral part of the polymer chain constituting the water gellant. The block copolymer may be a diblock copolymer or may contain three or more different blocks, so it is within the disclosure of this invention that in the block copolymer a multitude of blocks comprising the 4H-units are alternated in any fashion by a multitude of blocks that do not contain any 4H-unit. It is further preferred that the water gellants according to this third embodiment of the invention have a number average molecular weight of 1200-100,000, more preferably 2000-50000 and most preferably 7500-21000 Dalton.

The hydrophilic polymer according to the first preferred embodiment of the invention can be of natural origin or of synthetic origin. However, according to the invention, it is preferred that the hydrophilic polymer according to this first preferred embodiment of the invention is of synthetic origin.

If the hydrophilic polymer according to the first preferred embodiment is of natural origin, it is preferred that the hydrophilic polymer is selected from the group consisting of proteins, e.g. proteins selected from the group consisting of collagen, gelatine, or fibrin, and polysaccharides, e.g. polysaccharides selected from the group consisting of hyaluronate, agar, agarose, xantham gums, natural gum, alginate, chitosan or inulin, or synthetic derivatives from them, preferably collagen or chitosan. The water gellant according to this preferred embodiment of the invention has preferably a number average molecular weight of 1200-1,000,000, more preferably 2000-500000 and most preferably 7500-50000 Dalton.

If the hydrophilic polymer according to the first preferred embodiment is of synthetic origin, it is preferred that the polymer is obtainable by (co)polymerization of vinyl monomers. Preferably, these monomers are selected from the group consisting of:
(a) monomers according to the formula (8)

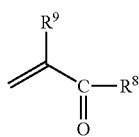

(8)

wherein $R^8$ is independently selected from the group consisting of:
(i) OH;
(ii) $C_1$-$C_{12}$ linear or branched alkoxy, optionally substituted with 1-6 hydroxy groups;
(iii) amide according to the formula —N($R^{10}$)$_2$ wherein $R^{10}$ can be hydrogen or $C_1$-$C_6$ linear or branched alkyl, optionally substituted with 1-6 hydroxy groups;
(iv) ammonium salt according to the formula —[N($R^{10}$)$_3$]$^+$ X$^-$, wherein $R^{10}$ is as defined for (iii) and X is a halogen atom; and
(v) a group according to the formula (9)

(9)

wherein $R^{10}$ is as defined for (iii) and p is 1-50 and q=2 or 3 and where (CH$_2$)$_q$ can be linear or branched; and wherein $R^9$ is hydrogen or methyl;

(b) $C_1$-$C_{12}$ linear or branched alkyl vinyl ether;
(c) vinyl alcohol;
(d) $C_2$-$C_{12}$ α-alkenylene ω-sulfonate having an alkaline earth metal cation or an alkali metal cation;
(e) $C_7$-$C_{12}$ vinylaryl sulfonate according to formula (10)

(10)

wherein $R^{10}$ is as defined for (iii) and M is an alkaline earth metal or an alkali metal cation;
(f) CH$_2$=CH—$R^{11}$, wherein $R^{11}$ is selected from the group consisting of pyrrolyl, imidazolyl, pyrazolyl, pyridinyl, pyrazinyl, pyrimidinyl, pyrrolidyl, indolyl, indolizinyl, indazolyl, purinyl, quinolizinyl, quinolinyl, isoquinolinyl, phthalizinyl, naphtypyridinyl, quinoxalinyl, quinazolinyl, cinnolinyl, pteridinyl, pyrrolidonyl, pyrrolinyl, pyrrolidinyl, imidazolidinyl, imidazolinyl, pyrazolidinyl, pyrazolinyl, piperidyl, piperazinyl, indolinyl, isoindolinyl, morpholinyl, isoxazolyl, furazinyl, and isothiazolyl;
(g) CH$_2$=CH—O—C(O)$R^{12}$, wherein R is selected from the group consisting of $C_1$-$C_6$ linear or branched alkyl;
(h) CH$_2$=CH—CH$_2$O$R^3$, wherein $R^{13}$ is selected from the group consisting of hydrogen and $C_1$-$C_6$ linear or branched alkyl; and
(i) N-vinyl lactams according to the formula (II)

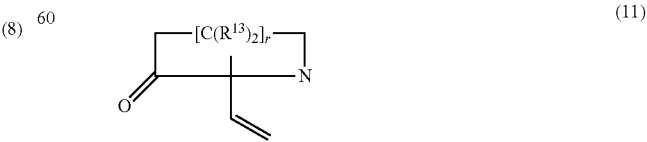

(11)

wherein $R^{13}$ is as defined for (h) and r is 2-6.

More preferably, these monomers are selected form groups (a) and (c), optionally copolymerised with groups (b), (d)-(i), most preferably this monomer is (a). The water gellant according to this preferred embodiment of the invention has a number average molecular weight of 1200-100,000, more preferably 2000-50000 and most preferably 7500-21000 Dalton.

The hydrophilic polymer according to the second preferred embodiment of the invention is preferably obtainable by polymerizing ethylene oxide, propylene oxide or a mixture thereof, using a multifunctional initiator as core molecule. Preferred examples of the hydrophilic polymer according to the second preferred embodiment of the present invention are telechelic poly(ethylene glycol) polymers having OH and/or $NH_2$ end-groups, poly(ethylene glycol) star polymers having OH and/or $NH_2$ end-groups, hyperbranched polymers having OH end-groups, e.g. Hybrane® from DSM, The Netherlands, and Boltorn® from Perstorp, Sweden, branched polyglycerols, and branched polyesters having OH end-groups.

Poly(ethylene glycol) star polymers having OH end-groups can for example be prepared by living anionic polymerization using divinyl benzene as the core molecule whereafter polyethylene oxide arms are grown outwards from the core. Other methods include the use of dendritic core molecules having a multitude of reactive groups from which polyethylene oxide arms can grow in outward direction. More simple initiators, e.g. glycerol and derivatives thereof or saccharoses, can be used as well as core molecule. Branched polyglycerols having OH end-groups can for example be obtained by Lewis acid catalyzed polymerization of glycidol. Branched polyesters can for example be prepared by polymerizing a dicarboxylic acid and/or a dicarboxylic anhydride, a diol such as polyethylene glycol and a multifunctional alcohol having at least three OH groups, e.g. trimethylol propane or glycerol. Even more preferably in this second preferred embodiment, is that the hydrophilic polymer is a poly(ethylene oxide) polymer having OH end-groups according to formula (12):

(12)

wherein Z represents the core molecule, r is in the range of 4 to 50 and s is in the range of 2 to 30, more preferably s is in the range of 2 to 15, and most preferably s is in the range of 3 to 12.

The hydrophilic polymer according to the third preferred embodiment of the invention is preferably selected from the group consisting of:
(a) polyether diols having a polyoxyalkylene structure and OH end-groups;
(b) polyesters and copolyesters having OH end-groups;
(c) polycarbonates and copolycarbonates having OH end-groups;
(d) polyorthoesters having OH end-groups;
(e) (hydrogenated) polyolefine diols; and
(f) polyurethanes; and
(g) polymers and copolymers based on combinations of these preferred polymers (a)-(e).

Although some of the above listed polymers (a)-(g) themselves may not be hydrophilic per se, copolymerizing them with the right amount of water soluble polymer and 4H-units can lead to a water gellant, as will be obvious to a person skilled in the art.

Examples of polymers (a) are polyetherdiols having a polyoxyalkylene structure and OH end-groups, e.g. polyethylene glycol, polypropylene glycol, poly(ethylene-co-propylene)glycol (random or block), polytetramethylene glycol. Examples of polymers (b) are polyesters and copolyesters made by polycondensation of dicarboxylic acids, e.g. adipic acid, and diols, e.g. 1,6-hexanediol, or by polycondensation of hydroxyacids, e.g. lactic acid; polyesters and copolyesters made by ringopening polymerisation of e.g. ∈-caprolactone, glycolide, lactide, δ-valerolactone, 1,4-dioxane-2-one, 1,5-dioxepan-2-one, oxepan-2,7-dione, and the like. Examples of polymers (c) are polycarbonates and copolycarbonates based on e.g. 1,6-hexanediol or glycol polycarbonate, polycarbonates and copolycarbonates made by ringopening polymerization of e.g. trimethylenecarbonate, 1,3-dioxepane-2-one, 1,3-dioxanone-2-one, 1,3,8,10-tetraoxacyclotetradecane-2,9-dione. An examples of polymers (d) is a polyorthoester based on e.g. 3,9-diethylene-2,4,8,10-tetraoxaspiro[5.5]undecane. Examples of polymers (e) are OH functionalized polybutadiene and OH functionalized (hydrogenated) poly(ethylene-butylene). An example of polymers (f) is polyurethane made by the reaction between polycaprolactondiol and hexane diisocyanate. An example of polymers (g) are OH functionalized block copolymers of polycaprolactone and polyethyleneglycol.

Preferably, the hydrophilic polymer according to this third preferred embodiment is selected from the group consisting of polyethylene glycol having OH end-groups or poly(ethylene-co-propylene)glycol—random or block—having OH end-groups according to formula (13):

(13)

wherein $R^{14}$ is hydrogen or methyl and t is 20-100, bifunctional polyesters prepared by polycondensation or ring opening polymerization, and polycarbonates made by ring opening polymerization. Most preferably, the hydrophilic polymer according to this third preferred embodiment is selected from the group consisting of polyethylene glycol having OH end-groups or poly(ethylene-co-propylene)glycol—random or block—having OH end-groups according to formula (13).

As an alternative, although less preferred, of the polymers according to formula (13), polyoxyalkylene amines having terminal amino groups, e.g. Jeffamines® sold by Huntsman, may be used.

The Hydrogel

In an embodiment of this invention, the water gellant comprises biodegradable moieties, that may be single bonds (e.g. an ester bond) or linkages or may be regions with multiple biodegradable bonds (e.g. a polyester or oligoester). The moieties may occur within parts of the hydrophilic polymer that do not comprise a 4H-unit, in the 4H-units themselves, and/or in the attachments between the hydrophilic polymer and the 4H-units. Examples of biodegradable bonds or linkages are covalent ester, thio-ester, ortho-ester, thio-ortho-ester, urethane, thio-urethane or amide bonds, but are preferably ester bonds.

The amount of the water gellant in the hydrogel ranges from 0.3%-50.0% by weight, preferably from 1%-40% by weight, more preferably from 4%-30% by weight, and most preferably from 5%-20% by weight, based on the total weight of the hydrogel. The hydrogel may contain additional functional ingredients that will contribute to the specific use of the hydrogel.

The hydrogel comprises 50.0 to 99.7 wt. % of water, preferably 60 to 99 wt. %, and most preferably 80 to 98 wt. %. based on the total weight of the hydrogel.

Obviously, the hydrogel may contain other polar solvents, preferably those solvents having a dielectric constant ∈ at 20°

C. of at least about 20. The upper limit is given by the dielectric constant ∈ at 20° C. for pure water which is about 80 (Handbook of Chemistry & Physics, $59^{th}$ Ed., page E-61, 1978-1979). Suitable examples are DMSO, alcohols, preferably ethanol and glycols, but more preferably ethanol and ketones, such as acetone. Preferably, the amount of other solvents is lower than 15% by weight, more preferably lower than 8% by weight, and most preferably lower than 2% by weight, calculated on the total weight of the hydrogel.

The hydrogels according to the present invention have a wide range of mechanical properties, ranging from elastic to tough, depending on the nature of the hydrophilic polymer and the number of 4H-units attached to the hydrophilic polymer. The reversible cross-links in the hydrogel allow for switching the gel into a liquid by the application of heat, changing the nature of the solvent or the concentration of the water gellant. Consequently, the processing or administration of the hydrogel can be done with processes known for liquids, like spraying or pumping. Preferably, the polymers present in the hydrogel have a relatively low number average molecular weight, preferably in the range from 1200 to 100000, more preferably from 2000 to 50000, most preferably from 7500 to 21000, in order to allow for easy solution processing of the water gellant, such as pumping or spraying.

The hydrogels can be used in cosmetic applications such as skin creams, anti-wrinkling compositions, pharmaceutical applications or biomedical applications such as controlled drug-delivery, tissue engineering, wound-dressings and wound-care, artificial articular cartilage material, soft contact lenses, tissue-adhesion, lubricating coatings for medical devices. superabsorbers, thickeners for aqueous solvents.

Although the present inventors do not wish to be bound to any theory on polymeric materials, it is believed that the mechanical strength and other material properties of the hydrogel are related to the nature of the polymer backbone, the amount of 4H-units per polymer chain and the way in which 4H-unit and the hydrophilic polymer are connected with one another. For example, it was found that the use of the hydrophilic polymers with a higher degree of polymerization generally resulted in more elastic materials, whereas hydrophilic polymers with a lower degree of polymerization generally resulted in tougher materials. Increasing the amount of 4H-units per polymer chain resulted in stronger, less tacky materials without the need for chemical cross-links or crystalline domains in the polymers. Consequently, these new hydrogels materials can be processed at relative low temperatures when compared to conventional hydrogels known in the art.

The hydrogels according to the present invention can be prepared by three different methods: (i) the hydrogel can be dissolved in aqueous solvent at elevated temperatures between 40° C. and 95° C., preferably between 60° C. and 90° C., followed by cooling down to temperatures between 0° C. and 40° C., preferably between 20° C. and 40° C.; (ii) the hydrogel can be swelled in aqueous solvent at temperatures between 0° C. and 60° C., preferably between 20° C. and 40° C.; and (iii) the hydrogel can be dissolved or dispersed in an organic water-miscible solvent, for example THF, acetone, MEK, alcohols, such as ethanol, DMSO, NMP, or solvent mixture, followed by the addition of water and subsequently the optional removal of the organic solvent with evaporation in vacuo or removal of the organic solvent by washing with water.

The hydrogels are applied in their gelled form after gelling the aqueous solvent with water gellant in a mould, eventually followed by cutting of the gel, or the water gellants are applied in their liquid state followed by gelling the polymers to a hydrogel after administration of the effective amount of the polymer to the desired site.

Additional ingredients in the hydrogels can be antioxidants, preservatives, fillers, salts, pH-buffers, dyes, bone-extracts, cosmetic active species, or bioactive species.

In a preferred embodiment of this invention, the hydrogels are used in cosmetic applications, such as anti-wrinkle creams, face-masks, mascara bases, dry-skin protectants and the like, substituting or adding to the gelatinous preparations that are commonly used.

In another preferred embodiment of this invention, the hydrogels are used in biomedical applications, such as carriers for the controlled release of drugs, scaffolds for tissue-engineering, or as adhesives or sealants for tissue. In these uses, the hydrogels also preferably comprise a biologically active or pharmaceutically active compound. The hydrogel may also comprise a bioactive species, e.g. a living cell, an enzyme, or a microorganism. A living cell in this embodiment means and includes individual animal and plant cells, cell clusters, tissues, organs and organisms, including organisms such as bacteria, fungi or moulds. A biologically active or pharmaceutically active compound, as used herein, includes a compound which provides a therapeutic, diagnostic, cosmetic, or prophylactic effect, a compound that affects or participates in tissue growth, cell growth, cell differentiation, a compound that may be able to invoke a biological action such as an immune response, or could play any other role in one or more biological processes. Such compounds, peptide or non-peptide, protein or non-protein, include, but are not limited to, antimicrobial agents (including antibacterial, hemotherapeutic and anti-fungal agents), anti-viral agents, anti-tumor agents, hormones, hormone antagonistics, corticosteroids such as mineralocorticosteroids or glucocorticosteroids, androgens, estrogens, progestins immunogenic agents, anti-inflammatory agents, anti-gout agents, centrally acting analgesics, local anesthetics, centrally active muscle relaxants, growth factors, (fluorescent) dyes, contrast agents, nucleic acids, lipids, lipopolysaccharides, (poly)saccharides, vitamins, and peptides, polypeptides and proteins in general.

Apart from the previous list, it is also possible to load the hydrogel with inorganic compounds, such as reactive oxygen scavengers and bone-extracts like apatite.

It is possible within the scope of the present invention to incorporate drugs of a polymeric nature, but also to incorporate drugs or vitamins of a relatively small molecular weight of less than 1500, or even less than 500.

Additionally, two or more different biologically active compounds may be present in the hydrogel. This is especially beneficial when the bioactivity is based on multivalent and/or synergistic interactions. A non-limiting example of such interaction is that cell adhesion is advantageously mediated by a combination of RGD and PHSRN peptides.

EXAMPLES

The following examples further illustrate the preferred embodiments of the invention. When not specifically mentioned, chemicals are obtained from Aldrich.

Example 1

Preparation of UPy1

1,6-Hexyldiisocyanate (650 g) and methylisocytosine (or 2-amino-4-hydroxy-6-methyl-pyrimidine, 65.1 g) were suspended in a 2-liter flask. The mixture was stirred overnight at 100° C. under an argon atmosphere. After cooling to room temperature, a liter of pentane was added to the suspension, while stirring was continued. The product was filtered, washed with several portions of pentane and dried in vacuum. A white powder was obtained. $^1$H NMR (400 MHz, CDCl$_3$): δ 13.1 (1H), 11.8 (1H), 10.1 (1H), 5.8 (1H), 3.3 (4H), 2.1 (3H), 1.6 (4H), 1.4 (4H). FT-IR (neat): ν (cm$^{-1}$) 2935, 2281, 1698, 1668, 1582, 1524, 1256.

Example 2

Preparation of UPy2

2-Amino-4-hydroxy-5-(2-hydroxy ethyl)-6-methyl-pyrimidine (12 gram) was suspended in IPDI (150 mL) and was stirred overnight at 90° C. under an argon atmosphere. A clear solution developed. The solution was cooled and precipitated in hexane. The solid was filtered, stirred in another portion of hexane, and then the product was isolated by filtration, washing with hexane and drying of the residue. Yield: 98%. $^1$H NMR (400 MHz, CDCl$_3$): δ 13.1 (1H), 11.9 (1H), 10.2 (1H), 4.8-4.5 (1H), 4.2 (2H), 4.0-3.2 (3H), 3.1-2.9 (3H), 2.7 (2H), 2.3 (3H), 1.9-1.6 (4H), 1.4-0.8 (26H). FT-IR (neat): ν (cm$^{-1}$) 2954, 2254, 1690, 1664, 1637, 1590, 1532, 1461, 1364, 1307, 1257, 1034, 791. MALDI-TOF-MS, [M$^+$]=614, [M+Na$^+$]=636.

Example 3

Preparation of UPy3

Methylisocytosine (5.2 g) was added to isophoronediisocyanate (IPDI, 50 mL) and subsequently stirred at 90° C. under an argon atmosphere for 3 days. The resulting clear solution was precipitated in heptane. The white gom was collected, heated in 150 mL heptane, cooled on ice, and filtered. The same procedure was repeated once more with the white residue, resulting in a white powder. $^1$H NMR (400 MHz, CDCl$_3$): δ 13.1 (1H), 12.0 (1H), 10.1 (1H), 5.9 (1H), 4.1-3.1 (3H), 2.1 (3H), 2.0-0.9 (15H). FT-IR (neat): ν (cm$^{-1}$) 2954, 2255, 1696, 1662, 1582, 1524, 1247.

Example 4 polyHEMA Based Hydrogel with 4H-Units

UPy1 (Example 1, 79 g) was suspended in chloroform (1.5 L), and thereafter hydroxy ethyl methacrylate (HEMA, 64 mL) and 15 drops of dibutyl tin dilaurate were added. The mixture was stirred at an oil bath temperature of 90° C. for 4 hours, and was then cooled and filtered. The filtrate was concentrated and dropped into an excess of diethylether. The white precipitate was collected by filtration, and was washed with diethylether. Drying in vacuo gave a white solid product (90 g) consisting of a methacrylate containing a 4H-unit. $^1$H NMR (400 MHz, CDCl$_3$): δ 13.1 (1H), 11.8 (1H), 10.1 (1H), 6.1 (1H), 5.8 (1H), 5.6 (1H), 5.0 (1H), 4.3 (4H), 3.3-3.2 (4H), 2.1 (3H), 1.9 (3H), 1.7-1.2 (8H). FT-IR (neat): n 3301, 2932, 1720, 1699, 1685, 1665, 1582, 1525, 1258.

This methacrylate containing 4H-unit (200 mg) was mixed together with HEMA (5 mL), AIBN (12 mg) and transfer agent mercapto ethanol (75 microliter) in DMF (15 mL), was degassed by purging with argon for 1 hr prior to polymerization. Polymerization was conducted at 80° C. for about 3 to 4 hours, after which the mixture was cooled down to room temperature and the polymer was recovered by precipitation into THF/hexane (3/1 v/v).

This polymer (250 mg) was dissolved in THF (1 μL) together with ethanol (0.1 mL), to this solution was added water (500 mg) followed by the evaporation of the organic solvents in vacuo, resulting in a hydrogel.

Example 5

Inuline-Based Hydrogel with 4H-Units

Inuline obtained from chicory (1.8 g, DP: 10-14) was dried in vacuo at 70° C. for 12 hours. The dried inuline was dissolved in dried NMP (10 mL) and heated to 70° C. resulting in a yellowish slightly turbid solution. Hereto was added UPy1 (0.98 g) and the reaction mixture was stirred for 12 h at 70° C. followed by the addition of water (60 mL) resulting in the formation of a hydrogel. The resulting hydrogel was subsequently rinsed 6 time with water (10 mL).

Example 6

Chitosan-Based Hydrogel with 4H-Units

High molecular weight chitosan was dissolved in water containing 5 wt % lactic acid, resulting in a solution with a total concentration of 5 wt % chitosan. This solution was diluted with DMSO to reach a total chitosan concentration of 1 wt %. To this solution was added UPy1 (0.3 equivalents compared to the number of repeating units in chitosan) and the mixture was subsequently vortexed and poured into a teflon mould, followed by curing at 75° C. for 1 h resulting in a clear gelled system. These gels are extracted 5 times with ethanol in order to remove the DMSO and to get clear rigid chitosan hydrogels.

Example 7

PEG-Star Hydrogel with 4H-Units

An 8-star poly(ethyleneglycol) with a total molecular weight of 10 kDa was obtained by ionic polymerization of ethylene-oxide using a initiator with 8 hydroxy-initiator sides based on a six-mer of glycerol. This PEG-star (1.0 g) was dried in vacuo at 80° C. for 12 h and subsequently dissolved in chloroform (50 mL) followed by the addition of UPy3 (278 mg) and 2 drops of dibutyltin dilaurate. The reaction mixture was heated to 80° C. and stirred for 8 hours, after which 4 drops of water were added. The reaction mixture was cooled down, filtered and precipitated in diethylether, resulting in a white precipitate. $^1$H NMR (400 MHz, CDCl$_3$): δ 13.1, 11.8, 10.1, 5.8, 5.0-4.6, 4.2, 3.8-2.8, 2.2, 1, 9-1.5, 1.4-0.8.

The resulting PEG-star containing 8 4H-units (200 mg) was dissolved in THF (1 mL) followed by the addition of water (1.8 mL), resulting in a clear solution. The THF was removed in vacuo whereupon a hydrogel was obtained.

Example 8

PEG-Block Copolymer Hydrogels with 4H-Units

General procedure illustrated for Example 8D: Telechelic hydroxy terminated PEG-6000 (10.20 g) was heated in vacuo in a 3-neck flask to 120° C. for 120 minutes (in example 8c and 8G a second telechelic polymer is added before this drying step) and subsequently cooled down to 80° C. UPy2 (1.25 g) and two drops of dibutyl tin dilaurate dissolved in toluene (40 mL) were added to the polymer melt and the solution was stirred overnight under argon at 80° C. The reaction mixture was diluted with 40 mL THF and precipitated into diethylether. The material is white (semi-crystalline), elastic and tough. $^1$H NMR (300 MHz, CDCl$_3$/CD$_3$OD): δ 4.1, 3.6, 2.8, 2.2, 1.8-1.4, 1.2-0.8.

The resulting PEG-UPy2 blockcopolymers were dissolved in THF (1 g/4 mL) to which the appropriate amount of water was added to get the right solids loading. These clear solutions were subsequently put in vacuo to remove the THF, resulting in the different hydrogels as described in Table 1.

This procedure was repeated for different polyethyleneglycols with different molecular weights, different ratios of UPy2, and different loadings of water gellant, as shown in table 1:

TABLE 1 different hydrogel formulations for example 8

| Example | Polymer 1$^a$ | Polymer 2 | Mole equivalents UPy2$^c$ | Solid Loading$^d$ | Hydrogel |
|---|---|---|---|---|---|
| 8A | PEG2000 | — | 1.10 | 4.5% | Soft/Flexible |
| 8B | PEG2000 | — | 1.32 | 5.8% | Flexible |
| 8C | PEG3000 | PCl2000$^b$ | 1.20 | 4.2% | Rigid |
| 8D | PEG6000 | — | 1.18 | 3.5% | Soft |
| 8E | PEG6000 | — | 1.32 | 7.2% | Elastic |
| 8F | PEG6000 | — | 1.32 | 3.2% | Visco-Elastic |
| 8G | PEG6000 | PEG1500 | 1.15 | 4.1% | Rigid |

$^a$PEGnnnn means Telechelic hydroxy terminated polyethyleneoxide with M$_n$ of nnnn; e.g. PEG2000 has a M$_n$ of 2 kg/mole.
$^b$PCl2000 is hydroxy-terminated polycaprolactone diol with M$_n$ = 2.1 kg/mole
$^c$mole equivalents are calculated based on the sum of both polymers in examples 8C and 8D
$^d$solid loading is weight of water gellant divided by the total weight of the hydrogel.

The invention claimed is:

1. A hydrogel composition comprising:
   (a) 0.3-50.0 wt. %, based on the total weight of the hydrogel composition, of a water gellant comprising a hydrophilic polymer to which at least two 4H-units are covalently attached, wherein the 4H-unit has the general formula (3) or formula (4) and tautomers thereof:

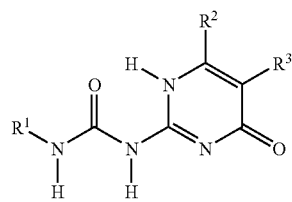

(3)

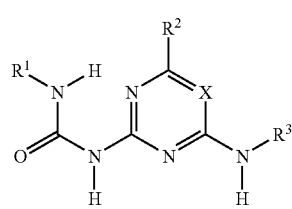

(4)

wherein X is nitrogen atom or a carbon atom bearing a substituent R$^{15}$, and
wherein the 4H-unit is bonded to a polymer backbone via R$^1$ and R$^2$ or via R$^1$ and R$^3$ with the other R groups representing, independently a side chain according to (i)-(viii);
(i) hydrogen;
(ii) C$_1$-C$_{20}$ alkyl;
(iii) C$_6$-C$_{12}$ aryl;
(iv) C$_7$-C$_{12}$ alkaryl;
(v) C$_7$-C$_{12}$ alkyl aryl;
(vi) polyester groups having the formula (5)

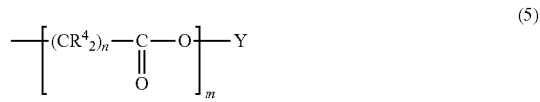

(5)

wherein R$^4$ and Y are independently selected from the group consisting of hydrogen and C$_1$-C$_6$ linear or branched alkyl, n is 1-6 and m is 10 to 100;
(vii) C$_1$-C$_{10}$ alkyl groups substituted with 1-4 ureido groups according to the formula (6):

R$^5$—NH—C(O)—NH— (6)

wherein R$^5$ is selected from the group consisting of hydrogen and C$_1$-C$_6$ linear or branched alkyl;
(viii) polyether groups having the formula (7)

(7)

wherein R$^6$, R$^7$ and Y are independently selected from the group consisting of hydrogen and C$_1$-C$_6$ linear or branched alkyl and o is 10-100;
(b) 50.0 to 99.7 wt. % water, based on the total weight of hydrogel;
(c) a polar solvent other than water, wherein the polar solvent comprises less than 15 wt. % of the total weight of the hydrogel composition; and
wherein components (a)-(c) form a hydrogel.

2. The hydrogel composition according to claim 1, wherein 2-50 4H-units are covalently attached to the hydrophilic polymer.

3. The hydrogel composition according to claim 1, wherein the water gellant is obtainable by functionalizing a hydrophilic homopolymer or a hydrophilic copolymer with 4H-units, independently selected from the group consisting of telechelic polymers, multifunctional polymers, functional star polymers, functional (hyper)branched polymers and functional dendritic polymers.

4. The hydrogel composition according to claim 3, wherein the water gellant derived from the multifunctional polymers has a number average molecular weight of 1200-1,000,000.

5. The hydrogel composition according to claim 3, wherein the water gellant derived from the telechelic polymers, the functional star polymers, the functional (hyper)branched polymers and the functional dendritic polymers has a number average molecular weight of 1200-100,000.

6. The hydrogel composition according to claim 3, wherein the water gellant derived from a block copolymer has a number average molecular weight of 1200-100,000.

7. The hydrogel composition according to claim 1, wherein the hydrophilic polymer is prepared from polymers obtainable by (co)polymerization of vinyl monomers, the vinyl monomers being selected from the group consisting of:

(a) monomers according to the formula (8)

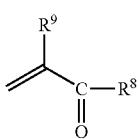

(8)

wherein $R^8$ is independently selected from the group consisting of:
(i) OH;
(ii) $C_1$-$C_{12}$ linear or branched alkoxy, optionally substituted with 1-6 hydroxy groups;
(iii) amide according to the formula —$N(R^{10})_2$ wherein $R^{10}$ can be hydrogen or $C_1$-$C_6$ linear or branched alkyl, optionally substituted with 1-6 hydroxy groups;
(iv) ammonium salt according to the formula —$[N(R^{10})_3]^+$ $X^-$, wherein $R^{10}$ is as defined for (iii) and X is a halogen atom; and
(v) a group according to the formula (9)

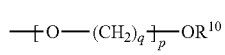

(9)

wherein $R^{10}$ is as defined for (iii) and p is 1-50 and q=2 or 3; and
wherein $R^9$ is hydrogen or methyl;
(b) $C_1$-$C_{12}$ linear or branched alkyl vinyl ether;
(c) vinyl alcohol;
(d) $C_2$-$C_{12}$ α-alkenylene ω-sulfonate having an alkaline earth metal cation or an alkali metal cation;
(e) $C_7$-$C_{12}$ vinylaryl sulfonate according to formula (10)

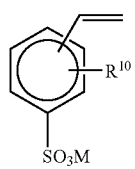

(10)

wherein $R^{10}$ is as defined for (iii) and M is an alkaline earth metal or an alkali metal cation;
$CH_2$=CH—$R^{11}$, wherein $R^{11}$ is selected from the group consisting of pyrrolyl, imidazolyl, pyrazolyl, pyridinyl, pyrazinyl, pyrimidinyl, pyrrolidyl, indolyl, indolizinyl, indazolyl, purinyl, quinolizinyl, quinolinyl, isoquinolinyl, phthalizinyl, naphtypyridinyl, quinoxalinyl, quinazolinyl, cinnolinyl, pteridinyl, pyrrolidonyl, pyrrolinyl, pyrrolidinyl, imidazolidinyl, imidazolinyl, pyrazolidinyl, pyrazolinyl, piperidyl, piperazinyl, indolinyl, isoindolinyl, morpholinyl, isoxazolyl, furazinyl, and isothiazolyl;
(g) $CH_2$=CH—O—$C(O)R^{12}$, wherein $R^{12}$ is selected from the group consisting of $C_1$-$C_6$ linear or branched alkyl;
(h) $CH_2$=CH—$CH_2OR^{13}$, wherein $R^{13}$ is selected from the group consisting of hydrogen and $C_1$-$C_6$ linear or branched alkyl; and (i) N-vinyl lactams according to the formula (II)

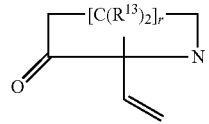

(11)

wherein $R^{13}$ is as defined for (h) and r is 2-6.

8. The hydrogel composition according to claim 1, wherein the hydrophilic polymer is prepared from poly(ethylene oxide) polymers having OH end-groups according to formula (12):

(12)

wherein r is in the range of 4 to 50 and s is in the range of 2 to 30.

9. The hydrogel composition according to claim 1, wherein the hydrophilic polymer is selected from the group consisting of polyethylene glycol having OH end-groups or poly(ethylene-co-propylene)glycol—random or block—having OH end-groups according to formula (13):

(13)

wherein $R^{14}$ is hydrogen or methyl and t is 20-100.

10. The hydrogel composition according to claim 1, wherein the hydrophilic polymer is selected from the group consisting of polyethylene glycol having OH end-groups or poly(ethylene-co-propylene) glycol—random or block—having OH end-groups according to formula (13) and wherein the hydrophilic polymer is additionally selected from the group consisting of polyesters and copolyesters having OH end-groups, or polycarbonates and copolycarbonates having OH end-groups, or polyorthoesters having OH end-groups.

11. The hydrogel composition according to claim 1, wherein the hydrogel comprises a biologically active or pharmaceutically active compound or a bioactive species.

12. The composition according to claim 1, wherein the 4H-unit is bonded to a polymer backbone via $R_1$ and $R_3$.

13. The composition according to claim 1, wherein the polar solvent comprises less than 2 wt. % of the total weight of the hydrogel composition.

14. A pharmaceutical composition comprising:
(a) 0.3-50.0 wt. %, based on the total weight of the pharmaceutical composition, of a water gellant comprising a hydrophilic polymer to which at least two 4H-units are covalently attached, wherein the 4H-unit has the general formula (3) or formula (4) and tautomers thereof:

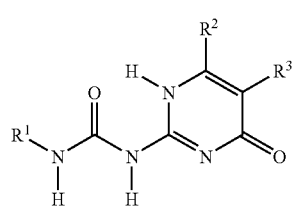

(3)

-continued

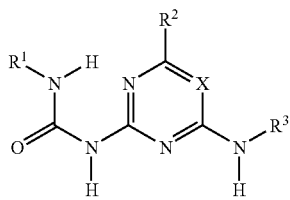

(4)

wherein X is nitrogen atom or a carbon atom bearing a substituent $R^{15}$, and
wherein the 4H-unit is bonded to a polymer backbone via $R^1$ and $R^2$ or via $R^1$ and $R^3$ with the other R groups representing, independently a side chain according to (i)-(viii);
(i) hydrogen;
(ii) $C_1$-$C_{20}$ alkyl;
(iii) $C_6$-$C_{12}$ aryl;
(iv) $C_7$-$C_{12}$ alkaryl;
(v) $C_7$-$C_{12}$ alkyl aryl;
(vi) polyester groups having the formula (5)

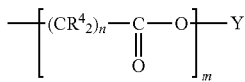

(5)

wherein $R^4$ and Y are independently selected from the group consisting of hydrogen and $C_1$-$C_6$ linear or branched alkyl, n is 1-6 and m is 10 to 100;
(vii) $C_1$-$C_{10}$ alkyl groups substituted with 1-4 ureido groups according to the formula (6):

(6)

wherein $R^5$ is selected from the group consisting of hydrogen and $C_1$-$C_6$ linear or branched alkyl;
(viii) polyether groups having the formula (7)

(7)

wherein $R^6$, $R^7$ and Y are independently selected from the group consisting of hydrogen and $C_1$-$C_6$ linear or branched alkyl and o is 10-100;
(b) 50.0 to 99.7 wt. % water, based on the total weight of pharmaceutical composition;
(c) a polar solvent other than water, wherein the polar solvent comprises less than 2 wt. % of the total weight of hydrogel;
(d) a biologically active or pharmaceutically active compound or a bioactive species; and
wherein components (a)-(d) form a hydrogel.

* * * * *